(12) United States Patent
Lott et al.

(10) Patent No.: US 6,242,178 B1
(45) Date of Patent: Jun. 5, 2001

(54) NUCLEIC ACID PROBES FOR DETECTING CANDIDA SPECIES

(75) Inventors: Timothy J. Lott; Cheryl M. Elie, both of Atlanta; Christine J. Morrison, Decatur; Errol Reiss, Chamblee, all of GA (US)

(73) Assignee: Centers for Disease Control and Prevention, Atlanta, GA (US)

( * ) Notice: Subject to any disclaimer, the term of this patent is extended or adjusted under 35 U.S.C. 154(b) by 0 days.

(21) Appl. No.: 08/903,446

(22) Filed: Jul. 30, 1997

(51) Int. Cl.[7] .............................. C12Q 1/68; C07H 21/02; C07H 21/04; C12N 15/00

(52) U.S. Cl. ............................ 435/6; 536/23.1; 536/24.3; 935/76; 935/77; 935/78

(58) Field of Search .............................. 435/6; 536/23.1, 536/24.3; 935/76, 77, 78

(56) References Cited

U.S. PATENT DOCUMENTS

| | | |
|---|---|---|
| 5,332,660 | 7/1994 | Takeda et al. . |
| 5,403,710 | 4/1995 | Weisburg et al. . |
| 5,405,745 | 4/1995 | Gorman et al. . |
| 5,426,026 | 6/1995 | Jordan . |
| 5,426,027 | 6/1995 | Lott et al. . |
| 5,489,513 | 2/1996 | Springer et al. . |
| 5,545,525 | 8/1996 | Montplaisir et al. . |
| 5,635,353 | 6/1997 | Lott et al. . |
| 5,645,992 | * 7/1997 | Lott et al. . |
| 5,688,644 | * 11/1997 | Lott et al. . |
| 5,707,802 | * 1/1998 | Sandhu et al. . |

FOREIGN PATENT DOCUMENTS

| | | |
|---|---|---|
| 2 734 844 | 12/1996 | (FR) . |
| 96 217 41 | 7/1996 | (WO) . |
| 98 11257 | 3/1998 | (WO) . |

OTHER PUBLICATIONS

Elie, C.M. et al., "Rapid Identification of Candida Species Using Species–Specific DNA Probes", Abstract of the General Meeting of the American Society for Microbiology, vol. 97, No. 0, 1997, p. 161.

Williams, D.W. et al., "Identification of Candida Species in Formalin Fixed, Paraffin Wax Embedded Oral Mucosa by Sequencing of Ribosomal DNA", Journal of Clinical Pathology: Molecular Pathology, vol. 49, 1996, pp. M–23–M28.

Nho, S. et al., "Species Differentiation by Internally Transcribed Spacer PCR and HhaI Digestion of Fluconazole–Resistant Candida Krusei, Candida Inconspicua, and Candida Norvegensis Strains", Journal of Clinical Microbiology, vol. 35, No. 4, 1997, pp. 1036–1039.

Lott, T.J. et al., "Sequence Analysis of the Internal Transcribed Spacer 2 (ITS2) from Yeast Species Within the Genus Candida", Current Microbiology, vol. 36, No. 2, 1998, pp. 63–69.

Reiss, E. et al., "Molecular Diagnosis and Epidemiology of Fungal Infections", Medical Mycology, vol. 36, No. Suppl., 1998, pp. 249–257.

Elie, C.M. et al., "Rapid Identification of Candida Species with Species–Specific DNA Probes", Journal of Clinical Microbiology, vol. 36, No. 11, 1998, pp. 3260–3265.

Sommer et al., Nucleic Acids Research 17 (16) :6749 (1989).*

Williams D. W., Genbank Accession Nos. L47114, and L47110 (Sep. 1995).*

Derek Sullivan et al., "Oligonucleotide Fingerprinting of Isolates of Candida Species Other than *C. albicans* and of Atypical Candida Species from Human Immunodeficiency Virus–Positive and AIDS Patients", *Journal of Clinical Microbiology*, vol. 31, No. 8, Aug. 1993, pp. 2124–2133.

Pamela Postlethwait et al., "Molecular Probe for Typing Strains of *Candida albicans*", *Journal of Clinical Microbiology*, vol. 34, No. 2, Feb. 1996, pp. 474–476.

Ilana Oren et al., "Isolation and Characterization of a species DNA probe for *Candida albicans*", *Nucleic Acids Research*, vol. 19, No. 25, 1991, pp. 7113–7116.

A. Carlotti et al., "Species–Specific Identification of *Candida krusei* by Hybridization with the CkF1,2 DNA Probe", *Journal of Clinical Microbiology*, vol. 34, No. 7, Jul. 1996, pp. 1726–1731.

Shawn R. Lockhart et al., "Most Frequent Scenario for Recurrent Candida Vaginitis Is Strain Maintenance with 'Substrain Shuffling': Demonstration by Sequential DNA Fingerprinting with Probes Ca3, CI, and Care2"; *Journal of Clinical Microbiology*, vol. 34, No. 4, Apr. 1996, pp. 767–777.

Timothy J. Lott et al., "Nucleotide Sequence Analysis of the 5–8S rDNA and Adjacent ITS2 Region of *Candida albicans* and Related Species", *Yeast*, vol. 9, 1993, pp. 1199–1206.

Shin–Ichi Fujita et al., "Microtitration Plate Enzyme Immunoassay to Detect PCR–Amplified DNA from Candida Species in Blood", *Journal of Clinical Microbiology*, vol. 33, No. 4, Apr. 1995, pp. 962–967.

* cited by examiner

Primary Examiner—W. Gary Jones
Assistant Examiner—Ethan Whisenant
(74) Attorney, Agent, or Firm—Jones & Askew, LLP

(57) ABSTRACT

The nucleic acid sequence encoding the internal transcribed spacer 2 region of Candida, the organism causing candidiasis, for various Candida species. Nucleic acid molecules useful as probes for detecting Candida species are described. The nucleic acid molecules are useful in methods for the detection and diagnosis of Candida infection in a sample or subject.

50 Claims, 4 Drawing Sheets

| FIGURE 1A | CA | CT | CG | CP | CK | GU | CR | CU | CZ | CH | LA | KF | VS | LU | NC |
|---|---|---|---|---|---|---|---|---|---|---|---|---|---|---|---|
| albicans | 0.426 / 0.275 | 0 | 0 | 0 | 0 | 0 | 0 | 0 | 0 | 0 | 0 | 0 | 0 | 0 | 0 |
| tropicalis | 0 | 0.870 / 0.354 | 0 | 0 | 0 | 0 | 0 | 0 | 0 | 0 | 0 | 0 | 0 | 0 | 0 |
| glabrata | 0 | 0 | 1.034 / 0.343 | 0 | 0 | 0.026 / 0.014 | 0 | 0 | 0.036 / 0.021 | 0 | 0 | 0 | 0 | 0 | 0 |
| parepsilosis | 0 | 0 | 0 | 0.493 / 0.231 | 0.025 / 0.018 | 0 | 0 | 0 | 0 | 0 | 0 | 0 | 0 | 0 | 0 |
| krusei | 0 | 0 | 0 | 0 | 0.389 / 0.136 | 0 | 0 | 0 | 0 | 0 | 0.114 / 0.042 | 0 | 0 | 0 | 0 |
| guilliermondii | 0 | 0 | 0 | 0 | 0 | 0.821 / 0.303 | 0 | 0 | 0.639 / 0.172 | 0 | 0 | 0 | 0 | 0 | 0 |
| rugosa | 0 | 0 | 0 | 0 | 0 | 0 | 0.222 / 0.098 | 0 | 0 | 0 | 0 | 0 | 0 | 0 | 0 |
| utilis | 0 | 0 | 0 | 0 | 0 | 0 | 0 | 1.161 / 0.193 | 0 | 0 | 0 | 0 | 0 | 0 | 0 |
| zeylannoides | 0 | 0 | 0 | 0 | 0 | 0 | 0 | 0 | 0.361 / 0.170 | 0 | 0 | 0 | 0 | 0 | 0 |
| haemulonii | 0 | 0 | 0 | 0 | 0 | 0 | 0 | 0 | 0 | 0.841 / 0.332 | 0 | 0 | 0 | 0 | 0 |
| lambica | 0 | 0 | 0 | 0 | 0 | 0 | 0 | 0 | 0 | 0 | 0.640 / 0.175 | 0 | 0 | 0 | 0 |
| kefyr | 0 | 0 | 0 | 0 | 0.037 / 0.008 | 0 | 0 | 0 | 0 | 0.014 / 0.009 | 0 | 1.184 / 0.384 | 0 | 0 | 0 |
| viswanathii | 0 | 0.175 / 0.093 | 0 | 0 | 0 | 0 | 0 | 0 | 0 | 0 | 0 | 0 | 0.988 / 0.419 | 0 | 0 |
| lusitaniae | 0 | 0 | 0 | 0 | 0 | 0 | 0 | 0 | 0 | 0 | 0 | 0 | 0 | 0.483 / 0.162 | 0 |
| norvegica | 0 | 0.015 / 0.028 | 0 | 0 | 0.019 / 0.032 | 0 | 0 | 0 | 0 | 0.013 / 0.024 | 0.017 / 0.019 | 0.012 / 0.013 | 0 | 0 | 0.258 / 0.102 |
| norvegensis | 0 | 0 | 0 | 0 | 0.014 / 0.021 | 0 | 0 | 0 | 0 | 0 | 0 | 0 | 0 | 0 | 0.014 / 0.018 |
| dubliniensis | 0 | 0 | 0 | 0 | 0 | 0 | 0 | 0 | 0 | 0 | 0 | 0 | 0 | 0 | 0 |
| pelliculosa | 0 | 0.024 / 0.011 | 0 | 0 | 0 | 0 | 0 | 0 | 0 | 0 | 0 | 0 | 0 | 0 | 0 |

FIGURE 1B

| | FA | NS | DUB | PEL |
|---|---|---|---|---|
| albicans | 0 | 0 | 0 | 0 |
| tropicalis | 0 | 0 | 0 | 0 |
| glabrata | 0.052<br>0.019 | 0 | 0 | 0 |
| parepsilosis | 0 | 0 | 0 | 0 |
| krusei | 0 | 0.085<br>0.045 | 0 | 0 |
| guilliermondii | 0.094<br>0.014 | 0 | 0 | 0.097<br>0.085 |
| rugosa | 0 | 0 | 0 | 0 |
| utilis | 0 | 0 | 0 | 0 |
| zeylannoides | 0 | 0 | 0 | 0 |
| haemulonii | 0 | 0 | 0 | 0 |
| lambica | 0 | 0 | 0 | 0 |
| kefyr | 0 | 0 | 0 | 0 |
| viswanathii | 0 | 0 | 0 | 0 |
| lusitaniae | 0 | 0 | 0 | 0 |
| norvegica | 0 | 0 | 0 | 0 |
| norvegensis | 0 | 0.716<br>0.242 | 0 | 0 |
| dubliniensis | 0 | 0 | 0.322<br>0.119 | 0 |
| pelliculosa | 0 | 0 | 0 | 0.624<br>0.320 |

| FIGURE 2A | FUM | FLAV | NID | TER | NIG | BLAS | HIST | Scere | Cr.hum | Cr.hum | Cr.na | Cr.nB | Cr.nC | Cr.nD | C.cat |
|---|---|---|---|---|---|---|---|---|---|---|---|---|---|---|---|
| albicans | neg | neg | 0 | 0 | 0 | neg | neg | neg | 0 | 0 | 0 | 0 | 0 | 0 | 0 |
| tropicalis | neg | neg | 0 | 0.114<br>0.052 | 0 | neg | neg | 0 | 0 | 0 | 0 | 0 | 0 | 0 | 0 |
| glabrata | 0 | 0 | 0 | 0 | 0 | 0 | 0 | 0.755<br>0.229 | 0 | 0 | 0 | 0 | 0 | 0 | 0 |
| parepsilosis | neg | 0 | 0 | 0 | 0 | neg | neg | neg | 0 | 0 | 0 | 0 | 0 | 0 | 0 |
| krusei | 0 | 0 | 0 | 0 | 0 | 0.071<br>0.025 | 0 | 0 | 0 | 0 | 0 | 0 | 0 | 0 | 0 |
| guilliermondii | 0 | 0 | 0 | 0.017<br>0.034 | 0 | 0 | 0 | 0 | 0 | 0 | 0.024<br>0.012 | 0.054<br>0.028 | 0.034<br>0.015 | 0.071<br>0.016 | 0 |
| rugosa | 0 | 0 | 0 | 0 | 0 | 0 | 0 | 0 | 0 | 0 | 0 | 0 | 0 | 0 | 0 |
| utilis | 0 | 0 | 0 | 0.147<br>0.035 | 0 | 0 | 0 | 0 | 0 | 0 | 0 | 0 | 0 | 0 | 0 |
| norvegica | 0 | 0 | 0 | 0 | 0 | 0 | 0.014<br>0.012 | 0 | 0 | 0 | 0 | 0 | 0 | 0 | 0.014<br>0.022 |
| norvegensis | 0 | 0 | 0 | 0 | 0 | 0 | 0 | 0 | 0 | 0 | 0 | 0 | 0 | 0 | 0 |
| dubliniensis | 0 | 0 | 0 | 0 | 0 | 0 | 0 | 0 | 0.041<br>0.019 | 0 | 0 | 0 | 0 | 0 | 0 |

FIGURE 2B

| | C.cat | S.cif | T.cut | Pmar |
|---|---|---|---|---|
| albicans | 0 | 0 | 0 | neg |
| tropicalis | 0 | 0 | 0 | neg |
| glabrata | 0 | 0 | 0 | 0 |
| parepsilosis | 0 | 0 | 0 | neg |
| krusei | 0 | 0 | 0 | 0 |
| guilliermondii | 0 | 0 | 0.039 0.029 | 0 |
| rugosa | 0 | 0 | 0 | 0 |
| utilis | 0 | 0 | 0 | 0 |
| norvegica | 0 | 0 | 0 | 0 |
| norvegensis | 0 | 0 | 0 | 0 |
| dubliniensis | 0 | 0 | 0 | 0 |

NUCLEIC ACID PROBES FOR DETECTING CANDIDA SPECIES

This invention was made by the Centers for Disease Control and Prevention, an agency of the United States Government.

TECHNICAL FIELD

The present invention relates in general to the field of microbiology. In particular, the invention relates to the species-specific detection of Candida, using DNA probes generated from the internal transcribed spacer 2 region of thirteen Candida species.

BACKGROUND OF THE INVENTION

Candidiasis is a fungal infection of mucosal membranes and other tissues. The infection is caused by the yeast-like organism Candida. Numerous species of Candida exist, including C. albicans. Rapid diagnosis of Candida infection has become important in recent years due to a substantial rise in the incidence of candidiasis. This increase in candidiasis is most likely caused by the rising incidence of AIDS, more intensive regimens of cancer therapy, complications of abdominal or cardio-thoracic surgery, organ transplantations, burns and trauma. While most candidiasis patients are infected with C. albicans, the number of non-C. albicans infections has been growing steadily and may reflect the increased use of azole drug prophylaxis and therapy since some non-C. albicans species are innately resistant to these drugs. Additional risk factors commonly associated with the onset of candidiasis include protracted, broad-spectrum antibiotic therapies, invasive devices, and prolonged hospital stays. Under these conditions, an antibiotic resistant replacement flora, including one or more Candida species, can proliferate in the gastrointestinal tract and invade from mucosal foci to deep tissues, especially when mucosal integrity has been disrupted as a result of chemotherapy or surgery. As the number of risk factors increases, the odds of developing candidiasis multiplies. (Jarvis, W. R. 1995. Epidemiology of nosocomial fungal infections, with emphasis on Candida species. Clin. Inf. Dis. 20:1526–30; Wenzel, R. P. 1995. Nosocomial candidemia: risk factors and attributable mortality. Clin. Inf. Dis. 20:1531–4; Wingard, J. R. 1995. Importance of Candida species other than C. albicans as pathogens in oncology patients. Clin. Inf. Dis. 20:115–25; and Fridkin, S. K. et al., 1996. Epidemiology of nosocomial fungal infections. Clin. Micro. Rev. 9:499–511).

Candida species such as C. glabrata and C. krusei are emerging as the causative agents of candidiasis possibly because these species are innately less susceptible to azole drugs. In addition, the ability of species such as C. parapsilosis to survive in the hospital environment increases the possibility of nosocomial transmission. Consequently, rapid identification to the species level is necessary for more timely, targeted, and effective antifungal therapy, and to facilitate hospital infection control measures.

Current methods available in the clinical laboratory to identify Candida species rely on morphology and assimilation tests. These tests require approximately three to five days to complete, sometimes requiring additional tests. (Warren, N. G. and K. C. Hazen, 1995. Candida, Cryptococcus, and other yeasts of medical importance, p. 723–737. In P. R. Murray, E. J. Barton, M. A. Pfaller, F. C. Tenover, and R. H. Yolken (ed.) Manual of Clinical Microbiology, 6th ed., American Society for Microbiology, Washington, D.C.)

U.S. Pat. No. 5,426,027, incorporated herein by reference, describes a method for detecting five species of Candida using the polymerase chain reaction (PCR) technique. The five species detected by the method are C. albicans, C. glabrata, C. tropicalis, C. parapsilosis, and C. krusei. U.S. Pat. No. 5,426,027 provides a rapid method for the isolation, release, purification, amplification and detection of DNA from the above-identified species of Candida from blood and other body fluids. The method uses universal fungal primers that amplify the multi-copy internal transcribed spacer 2 region (ITS2) of rDNA, located between the 5.8S and the 28S rDNA coding regions, to enhance the amount of Candida target DNA in samples. Once amplified, target DNA is hybridized to probes which are then used in a microtitration plate format for the identification of specific species of Candida. However, the method described in U.S. Pat. No. 5,426,027 is incapable of differentiating between Candida species other than those listed above.

Due to the increase in infections caused by other species of Candida, and the differences in therapeutic strategies for treating candidiasis caused by various Candida species, it is desirable to have a method for detecting and differentiating additional Candida species.

Therefore, there is a need for sensitive, rapid, species-specific methods for the detection of Candida. In addition, there is a need for universal fungal primers to amplify all fungal DNA followed by species-specific probes for Candida to be used in detection methods and as scientific research tools to investigate the Candida organism and to implement appropriate therapies and treatments for candidiasis.

SUMMARY OF THE INVENTION

Isolated nucleic acid molecules that selectively hybridize with nucleic acid molecules encoding the internal transcribed spacer 2 (ITS2) region of various species of Candida, or complementary sequences thereof, are described herein. The nucleic acid molecules are useful as probes to detect the presence and identity of a Candida species in a sample or specimen with high sensitivity and specificity. The nucleic acid molecules are also useful as laboratory research tools to study the organism and related diseases and to guide therapies and treatments for those diseases. In addition, methods are described for the detection of and differentiation between Candida species.

The Candida species detected by the probes and methods described herein include C. guilliermondii, C. haemulonii, C. kefyr, C. lambica, C. lusitaniae, C. norvegensis, C. norvegica, C. rugosa, C. utilis, C. viswanathii, C. zeylanoides, C. dubliniensis, and C. pelliculosa. The method provides a simple, rapid, and feasible means for identifying and distinguishing these Candida species in clinical laboratories.

Therefore, it is an object of the present invention to provide probes and sensitive methods for detecting and differentiating Candida organisms in clinical and laboratory settings.

It is a further object of the present invention to provide nucleic acid probes specific for various Candida species.

It is a further object of the present invention to provide species-specific nucleic acid probes that hybridize to the internal transcribed spacer 2 region of particular Candida species.

It is a further object of the present invention to provide simple, rapid and reliable methods for detecting, diagnosing, or monitoring the progress of therapy for diseases caused by Candida organisms.

It is a further object of the invention to provide methods for detecting Candida in a tissue specimen or biological fluid sample of an infected patient, including a blood sample, or in cultures of Candida from any source.

These and other objects, features, and advantages of the present invention will become apparent after a review of the following detailed description of the disclosed embodiments and the appended claims.

BRIEF DESCRIPTION OF THE DRAWINGS

FIG. 1 is a chart showing absorbance values for the hybridization of eighteen species-specific probes to DNA from the same Candida species, other Candida species, and other fungal organisms. The vertical axis identifies the Candida species name of the probe. The horizontal axis identifies the DNA using a two or three letter abbreviation. Ca is an abbreviation for *C. albicans*. Ct is an abbreviation for *C. tropicalis*. Cg is an abbreviation for *C. glabrata*. Cp is an abbreviation for *C. parapsilosis*. Ck is an abbreviation for *C. krusei*. Gu is an abbreviation for *C. guilliermondii*. Cr is an abbreviation for *C. rugosa*. Cu is an abbreviation for *C. utilis*. Cz is an abbreviation for *C. zeylanoides*. Ch is an abbreviation for *C. haemulonii*. La is an abbreviation for *C. lambica*. Kf is an abbreviation for *C. kefyr*. Vs is an abbreviation for *C. viswanathii*. Lu is an abbreviation for *C. lusitaniae*. Nc is an abbreviation for *C. norvegica*. Fa is an abbreviation for *C. famata*. Ns is an abbreviation for *C. norvegensis*. Dub is an abbreviation for *C. dubliniensis*. Pel is an abbreviation for *C. pelliculosa*. Upper values in each grid are provided as a mean absorbance at $A_{650\ nm}$. The lower value in each grid represents the standard deviation from the mean absorbance for all samples tested. The absorbance value "0" represents Mean $A_{650\ nm} \leq 0.010$.

FIG. 2 is a chart showing absorbance values for the hybridization of eleven species-specific probes to DNA from other Candida species and other fungal organisms. The vertical axis identifies the Candida species name of the probe. The horizontal axis identifies the DNA using a three to five letter abbreviation. Fum is an abbreviation for *Aspergillus fumigatus*. Flav is an abbreviation for *Aspergillus flavus*. Nid is an abbreviation for *Aspergillus nidulans*. Ter is an abbreviation for *Aspergillus terreus*. Nig is an abbreviation for *Aspergillus niger*. Blas is an abbreviation for *Blastomyces dermatitidis*. Hist is an abbreviation for *Histoplasma capsulatum*. Scere is an abbreviation for *Saccharomyces cerevisiae*. Cr.hum is an abbreviation for *Cryptococcus humicolus*. Cr.na is an abbreviation for *Cryptococcus neoformans*, Serotype A. Cr.nb is an abbreviation for *Cryptococcus neoformans*, Serotype B. Cr.nc is an abbreviation for *Cryptococcus neoformans*, Serotype C. Cr.nd is an abbreviation for *Cryptococcus neoformans*, Serotype D. C.cat is an abbreviation for *Candida catenulata*. S.cif is an abbreviation for *Stephanoascus ciferrii*. T.cut is an abbreviation for *Trichosporon cutaneum*. Pmar is an abbreviation for *Penicillium marneffei*. Upper values in each grid are provided as a mean absorbance at $A_{650\ nm}$. The lower value in each grid represents the standard deviation from the mean absorbance for all samples tested. The absorbance value "0" represents Mean $A_{650\ nm} \leq 0.010$. The term "Neg" denotes negative detection as previously reported by Fujita, et al., 1995. *J. Clin. Microbiol.* 33:962–967.

DETAILED DESCRIPTION OF THE INVENTION

Nucleic acid molecules that selectively hybridize to all or a portion of the internal transcribed spacer 2 (ITS2) region of various Candida species are provided. The sequences of nucleic acid molecules encoding the ITS2 region of *C. guilliermondii, C. haemulonii, C. kefyr, C. lambica, C. lusitaniae, C. norvegensis, C. norvegica, C. rugosa, C. utilis, C. viswanathii, C. zeylanoides, C. dubliniensis,* and *C. pelliculosa* are set forth as SEQ ID NOs:1–13.

The nucleic acid molecules described herein are useful as probes to detect, identify, and distinguish or differentiate between Candida species in a sample or specimen with high sensitivity and specificity. The probes can be used to detect the presence of Candida in the sample, diagnose infection with the disease, quantify the amount of Candida in the sample, or monitor the progress of therapies used to treat the infection. The nucleic acid molecules are also useful as laboratory research tools to study the organism and the disease and to guide therapies and treatments for the disease.

Exemplary nucleic acid probes that selectively hybridize with nucleic acid molecules encoding the ITS2 region of the thirteen species of Candida identified above are set forth as SEQ ID NOs:22–35. Additional probes that selectively hybridize to the ITS2 region of the Candida species described herein can be identified by those skilled in the art using routine screening procedures as set forth in more detail below.

Detection of DNA or RNA by the probes is facilitated by means such as nucleic acid amplification including the polymerase chain reaction (PCR) or ligase chain reaction (LCR), for example. Alternatively, the probe is labeled with a detectable label and detected in accordance with methods well known to those skilled in the art.

The term "isolated" in the context of a compound, such as a nucleic acid, is defined herein as free from at least some of the components with which the compound naturally occurs. A nucleic acid which "selectively hybridizes" is defined herein as a nucleic acid that hybridizes to a species-specific portion of a Candida ITS2 region nucleic acid, and does not hybridize with other nucleic acids so as to prevent determination of an adequate positive hybridization to the species-specific portion of the Candida ITS2 region. Therefore, in the design of hybridizing nucleic acid probes, selectivity will depend upon the other components present in a sample. The hybridizing nucleic acid probe should have at least 70% complementarity with the segment of the nucleic acid to which it hybridizes. As used herein to describe nucleic acid probes, the term "selectively hybridizes"

excludes the occasional randomly hybridizing nucleic acids, and thus, has the same meaning as "specifically hybridizes." The selectively hybridizing nucleic acids of the invention can have at least 70%, 80%, 85%, 90%, 95%, 97%, 98%, and 99% complementarity with the segment of the sequence to which it hybridizes. Hybridization studies are preferably conducted under stringent hybridization conditions.

Candida Probes

Nucleic acid molecules having the sequences set forth as SEQ ID NOs: 1–13, or complementary sequences thereof, will selectively hybridize to ITS2 DNA or RNA from each respective Candida species. For example, a nucleic acid molecule having the sequence of SEQ ID NO: 1 will selectively hybridize to ITS2 DNA from C. guilliermondii under stringent hybridization conditions and will not hybridize under the same or similar conditions to ITS2 DNA from any of the other twelve Candida species set forth above. Similarly, nucleic acid molecules having the sequences set forth as SEQ ID NOs: 22–35, and complementary sequences thereof, will selectively hybridize under stringent hybridization conditions to ITS2 DNA from each respective Candida species. Nucleic acid molecules having the sequences set forth as SEQ ID NOs: 22–35 represent portions or fragments of the corresponding nucleic acid molecules having the sequences set forth as SEQ ID NOs: 1–13. Two exceptions include the cross-reactivity of the C. guillermondii probe (SEQ ID NO: 22) with C. zeylanoides DNA and the C. glabrata probe (SEQ ID NO: 19) with S. cerevisiae DNA. The C. zeylanoides probe (SEQ ID NO: 25) does not cross-react with C. guillermondii DNA, however, so that, by a process of elimination, these two species can be differentiated using these probes. No probe for S. cerevisiae has been developed to date, but given the rare occurrence of this organism in infected patients and that drug therapy would be the same for both C. glabrata and S. cerevisiae infections (both azole resistant), the cross-reactivity of the C. glabrata probe with S. cerevisiae does not pose a clinical problem.

It will be understood that the probes provided herein are merely exemplary and that those skilled in the art could identify additional portions or fragments of each ITS2 sequence to be used as species-selective probes without undue experimentation from the sequences provided in SEQ ID NOs:1–13, or complementary sequences thereof, which hybridize with specificity to each Candida species respectively. Therefore, the probes shown in SEQ ID NOs: 22–35 are only provided as examples of probes specific for Candida that can be derived from the ITS2 regions of each species in SEQ ID NOs:1–13, respectively. The ITS2 region for each Candida species offers a number of very unusual sequences for use as PCR primers. Therefore, comparisons can be made between the Candida ITS2 sequence of two or more species to identify unique or non-homologous regions that would be useful to construct probes that would be specific for distinguishing between those Candida and have minimal cross-hybridization with ITS2 regions from other species. One useful computer program for generating selective probes is the Gene Jockey program available from Biosoft (Cambridge, UK).

The invention contemplates sequences, probes, and primers that selectively hybridize to the DNA or the complementary, or opposite, strand of DNA as those specifically provided herein. Specific hybridization with nucleic acid can occur with minor modifications or substitutions in the nucleic acid, so long as functional species-specific hybridization capability is maintained.

The term "probe" is defined herein to include nucleic acid sequences that can be used as primers for selective hybridization with complementary nucleic acid sequences for their detection or amplification. Therefore, the terms "probe" or "probes" as used herein are defined to include primers. Such probes can vary in length from about 5 to 263 nucleotides, or preferably from about 10 to 50 nucleotides, or most preferably about 18–26 nucleotides. Isolated nucleic acids are provided herein that selectively hybridize with the species-specific nucleic acids under stringent conditions and should have at least 5 nucleotides complementary to the sequence of interest. See generally, Sambrook, J., et al., 1989. Molecular cloning: a laboratory manual, latest edition. Cold Spring Harbor Laboratory, Cold Spring Harbor, N.Y.

If used as primers, the invention also preferably provides compositions including at least two nucleic acids which hybridize with different regions so as to amplify a desired region. Depending on the length of the probe or primer, the target region can range between 70% complementary bases and full complementarity and still hybridize under stringent conditions. For example, when diagnosing the presence of a Candida species, the degree of complementarity between the hybridizing nucleic acid (probe or primer) and the sequence to which it hybridizes (e.g., Candida DNA from a sample) is at least enough to distinguish hybridization with a nucleic acid from other yeasts and filamentous fungi.

It may be desirable in some cases to construct probes from the ITS2 regions disclosed herein which can selectively hybridize with more than one Candida species, but that still do not hybridize with other species of Candida. Such probes are, therefore, useful for detecting a selective sub-group of one or more species within the Candida genus. Examples of nucleic acids unique to each species of Candida are provided in the listed sequences so that the degree of complementarity required to distinguish selectively hybridizing from nonselectively hybridizing nucleic acids under stringent conditions can be clearly determined for each nucleic acid.

Methods for the Detection and Identification of Candida

Methods of using the nucleic acids described herein to detect and identify the presence of Candida are also provided. The method involves the steps of obtaining a sample suspected of containing Candida. The sample may be a biological fluid or tissue specimen taken from an individual, such as blood, saliva, vaginal mucosa, tissues, etc. Alternatively the sample may be taken from the environment, such as a swab of a potentially contaminated surface. The Candida cells in the sample are then lysed, and the DNA extracted and precipitated. The DNA is preferably amplified using universal primers derived from the genomic regions adjacent to or including portions of the ITS2 region of the Candida DNA sequence. Examples of such primers are described below. Detection of Candida DNA is achieved by hybridizing the amplified DNA with a Candida species-specific probe that selectively hybridizes with the DNA. Detection of hybridization is indicative of the presence of Candida.

Preferably, detection of nucleic acid hybridization with probes can be facilitated by the use of detectable moieties well known to those skilled in the art. For example, the probes can be labeled with digoxigenin and biotin and used in a streptavidin-coated microtiter plate assay where an enzymatically labeled antibody to digoxigenin and a colorimetric substrate allows for detection. Other detectable moieties include radioactive labeling, enzyme labeling, and fluorescent labeling, for example.

Candida Detection Kit

The invention further contemplates a kit containing one or more Candida ITS2 specific nucleic acid probes that can be used for the detection of Candida organisms in a sample. Such a kit can also contain the appropriate reagents for lysing cells, amplifying DNA, hybridizing the probe to the sample, and detecting bound probe.

EXAMPLE 1

Cloning and Sequencing of the ITS2 Region from Candida

This example describes the cloning and sequencing of the ITS2 region from various species of Candida. The organisms used in this example and their sources are listed below in Table 1. Isolates of Candida spp., *Cryptococcus humicolus*, *Stephanoascus ciferrii*, and *Trichosporon cutaneum* were grown in 10 ml of YPD broth (1% yeast extract, 2% Bacto Peptone, 1% glucose; Difco Laboratories, Detroit, Mich.) at 35° C. for 18 hours. *Cryptococcus neoformans*, serotypes A, B, C, and D were grown in YPD broth+2.9% NaCl at 35° C. for 18 hours to reduce capsule formation. All broth cultures were grown on a gyrarotary shaker at 150 rpm.

TABLE 1

Microorganisms tested against all probes.

| Organism | Number | Source |
|---|---|---|
| Candida albicans | B311 | Human |
| Candida tropicalis | CDC 38 | Reference strain |
| Candida glabrata | Y-65 | Type culture, feces |
| Candida parapsilosis | ATCC 22019 | Type culture, sprue |
| Candida krusei | CDC 259-75 | Reference strain |
| Candida guilliermondii | ATCC 6260 | Type culture, bronchitis |
| Candida rugosa | ATCC 10571 | Type culture, human feces |
| Candida utilis | ATCC 22023 | Type culture, factory |
| Candida zeylanoides | ATCC 7351 | Type culture, blastomycotic macroglossia |
| Candida haemulonii | ATCC 22991 | Type culture, gut contents of fish |
| Candida lambica | ATCC 24750 | Type culture, beer |
| Candida kefyr | ATCC 46764 | Clinical isolate |
| Candida viswanathii | ATCC 22981 | Type culture, cerebrospinal fluid |
| Candida lusitaniae | ATCC 34449 | Type culture, pig |
| Candida norvegica | ATCC 36586 | Type culture, sputum |
| Candida norvegensis | ATCC 22977 | Type culture, sputum |
| Candida pelliculosa | ATCC 8168 | Type culture |
| Candida dubliniensis | CBS 7987 | Type culture, human tongue |
| Candida famata | ATCC 36239 | Type culture |
| Aspergillus fumigatus | ATCC 36607 | Clinical isolate |
| Aspergillus flavus | ATCC 11497 | Environmental isolate |
| Aspergillus nidulans | ATCC 10074 | unspecified |
| Aspergillus terreus | ATCC 7860 | unspecified |
| Aspergillus niger | ATCC 16404 | Environmental isolate |
| Blastomyces dermatitidis | CDC B4478 | Dog |
| Histoplasma capsulatum | G217B | Human |
| Saccharomyces cerevisae | AB 972 | unspecified |
| Cryptococcus humicolus | ATCC 14438 | Type culture, soil |
| Cryptococcus humicolus | ATCC 38294 | Human leg |
| Cryptococcus neoformans, Serotypes A, B, C, D | A = 9759-MU-1, B = BIH409, C = K24066TA N, D = 9375 | Reference Strains from Dr. Cherniak, GA. State Univ. |
| Candida catenulata | ATCC 18812 | Perleche |
| Candida catenulata | ATCC 10565 | Type culture, human feces |
| Stephanoascus ciferrii | ATCC 22873 | Type culture of Candida ciferrii, neck of cow |
| Trichosporon cutaneum | ATCC 34148 | Clinical isolate |
| Penicillin marneffei | CDC B3420 | Human lymph node |

DNA Isolation

DNA was extracted from all species using the Puregene Gram Positive Bacteria and Yeast DNA Isolation Kit (Gentra, Inc., Research Triangle Park, North Carolina). DNA from filamentous and dimorphic fungi was obtained as described by Fujita, S.-I., et al., 1995, Microtitration plate enzyme immunoassay to detect PCR-amplified DNA from Candida species in blood. *J. Clin. Microbiol.* 33:962–967, or was a gift from Dr. Liliana de Aguirre, CDC Mycotic Diseases Laboratories, Atlanta, Ga. Quantification of the DNA was performed on a fluorometer (Dyna Quant 200) using Hoechst 33258 Dye (Pharmacia Biotech, Piscataway, N.J.). DNA was diluted in TE buffer (10 mM Tris-Cl, 1 mM EDTA) so that 1 ng of template DNA was added to each PCR reaction vial.

Oligonucleotide Synthesis of Primers and Probes

Oligodeoxyribonucleotide primers and probes (Table 2) were synthesized as described by Fujita, 1995, *J. Clin. Microbiol.* 33:962–967. The universal fungal primers ITS3 and ITS4, as described by White et al., were used to amplify the ITS2 region. (White, T. J., et al., 1990, Amplification and direct sequencing of fungal ribosomal RNA genes for phylogenetics, p.315–322. In M. A. Innis, et al., (ed.), PCR protocols. Academic Press, San Diego, Calif.)

The 5.8S rDNA universal 5' primer (ITS3) has the following sequence:

5'GCA TCG ATG AAG AAC GCA GC 3' (SEQ ID NO: 14)

The 28S rDNA universal 3' primer (ITS4) has the following sequence:

5'TCC TCC GCT TAT TGA TAT GC 3'(SEQ ID NO: 15)

The 5.8S rDNA 5'-end-labeled, biotinylated probe (universal capture probe) has the following sequence:

5'Bio-CA TGC CTG TTT GAG CGT CRT T 3' (SEQ ID NO: 16)

The sequenced ITS2 regions were determined to be as follows:

*Candida guilliermondii* (SEQ ID NO:1)

```
CTCTCTCAAA CCCCCGGGTT TGGTATTGAG TGATACTCTT AGTCGGACTA GGCGTTTGCT    60
TGAAAAGTAT TGGCATGGGT AGTATGGATA GTGCTGTCGA CCTCTCAATG TATTAGGTTT   120
ATCCAACTCG TTGAATGGTG TGGCGGGATA TTTCTGGTAT TGTTGGCCCG GCCTTACAAC   180
AACCAAACAA GC                                                       192
```

*Candida haemulonii* (SEQ ID NO:2)

```
GAGCGTGATA TCTTCTCACC GTTGGTGGAT TTGTTTCTAA ATATCATGCC ACAGTGAAGT    60
CTACGC                                                               66
```

*Candida kefyr* (SEQ ID NO:3)

```
CTCTCTCAAA CCTTTGGGTT TGGTAGTGAG TGATACTCGT CTCGGGCTTA ACTTGAAAGT    60
GGCTAACCGT TGCCATCTGC GTGAGCAGGC TGCGTGTCAA GTCTATGGAC TCGACTCTTG   120
CACATCTACG TCTTAAGTAT GCGCCAATTC GTGGTAAGCT TGGGTCATAG AGACTCATAG   180
GTGTTATAAA GACTCGCTGG TGTTTGTCTC CTTGAGGCAT ACGGCTTTAC AACTCTCAAG   240
```

*Candida lambica* (SEQ ID NO:4)

```
CCTTCTTGGA GCGGTGCTTC AGACCTGGCG GGCTGTCTTT TTGGACGGCG CGCCCAAAGC    60
GAGGGGCCTT CTGCGCGAAC TAGACTGTGC GCGCGGGGCG GTCGGCGAAC TTATTACCAA   120
G                                                                    121
```

*Candida lusitaniae* (SEQ ID NO:5)

```
GAGCGTCGCA TCCCCTCTAA CCCCCGGTTA GGCGTTGCTC CGAAATATCA ACCGCGCTGT   60
CAAATACG                                                             68
```

*Candida norvegensis* (SEQ ID NO:6)

```
CCTTCTTGCG CAAGCAGAAG TTGGGGTTGC CACGGCCCGT GCGGCCTGTG TGTGGCTCCC    60
CGAAACGGAA CGGCAGCGGG ACTGAGCGAA GTACACAACA CTCGCGCTTG GCCCGCCGAA   120
CTTTTTTTTA ATCTAAG                                                  137
```

*Candida norvegica* (SEQ ID NO:7)

```
CCTTCTCAAG CGTGAGCTTG GTGTTGGCGG AGGTCTTTCG AGGCCCCGCT GAAATACGCA    60
GGGGGTGCGT GGAAACGAGC TTTCTCTCTA CTAATGTCTA GTTCTGCCAA CTCATTGGAC   120
GAGCGTCTGC TGGCTCCACA ATCCCACCCC CATTACCCCA AC                      162
```

*Candida rugosa* (SEQ ID NO:8)

```
CTCTCTCGCA AGTGTTGGCA CCACGCCGGC AGGCGTCTGC CCGAAACGCG ACCGTCTAAA   60
ACAGTTAAGC TTGTTACAGA CTCACGATC                                    89
```

*Candida utilis* (SEQ ID NO:9)

```
CTCTCTCAAG ATCCTCTAGG GGACTTGGTA TTGAGTGATA CTCTGTGTTA ACTTGAAATA   60
CTCTAGGCAG AGCTCCCCCC TGGAAATCCT CTGGGCCGAA ATAATGTATT AGGTTCTACC  120
AACTCGTTAT TTTCCAGACA GACTTCCAGG CAGAGCTCGT GCCCCTAACA TAGCAGTCTA  180
AGC                                                                183
```

*Candida viswanathii* (SEQ ID NO:10)

```
CTCCCTCAAC CCCGCGGGTT TGGTGTTGAG CAATACGCCA GGTTTGTTTG AAAGACGTAC   60
GTGGAGACAA TATTAGCGAC TTAGGTTCTA CCAAAACGCT TGTGCAGTCG GTCCCACACA  120
CAGTGTAAGC TAACA                                                   135
```

*Candida zeylanoides* (SEQ ID NO:11)

```
CTCTCTCAAA TCTTCGGATT TGGTTTTGAG TGATACTCTT AGTCAGACTA AGCGTTTGCT   60
TGAAATGTAA TGGCATGAGT GGTACTAGAT AGTGCTGAAC TGTCGTCATG TATTAGGTTT  120
ATCCAACTCG TTGACCAGTA TAGTATTTGT TTATTACACA GGCTCGGCCT TACAACAACA  180
AACAAAG                                                            187
```

*Candida dubliniensis* (SEQ ID NO:12)

```
CTCCCTCAAA CCCCTAGGGT TTGGTGTTGA GCAATACGAC TTGGGTTTGC TTGAAAGATG   60
ATAGTGGTAT AAGGCGGAGA TGCTTGACAA TGGCTTAGGT GTAACCAAAA ACATTGCTAA  120
GGCGGTCTCT GGCGTCGCCC ATTTTATTCT TCAAAC                            156
```

*Candida pelliculosa* (SEQ ID NO:13)

```
CTCTCTCAAA CCTTCGGGTT TGGTATTGAG TGATACTCTG TCAAGGGTTA ACTTGAAATA   60
TTGACTTAGC AAGAGTGTAC TAATAAGCAG TCTTTCTGAA ATAATGTATT AGGTTCTTCC  120
AACTCGTTAT ATCAGCTAGG CAGGTTTAGA AGTATTTTAG GCTCGGCTTA ACAACAATAA  180
ACTAAAAG                                                           188
```

EXAMPLE 2

Species-Specific detection of Candida
Synthesis of Oligonucleotide Probes

Oligonucleotide probes were designed from sequence data for the ITS2 region of Candida spp rDNA. (Lott, T. J., et al., 1997. Sequence analysis of the internal transcribed spacer 2 (ITS2) from yeast species within the genus Candida. Current Microbiology, in press).

TABLE 2

Synthetic Oligonucleotides used in PCR and hybridization analyses

| Nucleotide sequence (5' to 3') and Chemistry | Primer or Probe | Source |
|---|---|---|
| *Dig-AT TGC TTG CGG CGG TAA CGT CC | SEQ ID NO: 17 | ITS2 region of *C.albicans* |
| Dig-AA CGC TTA TTT TGC TAG TGG CC | SEQ ID NO: 18 | ITS2 region of *C. tropicalis* |
| Dig-TT TAC CAA CTC GGT GTT GAT CT | SEQ ID NO: 19 | ITS2 region of *C. glabrata* |
| Dig-AC AAA CTC CAA AAC TTC TTC CA | SEQ ID NO: 20 | ITS2 region of *C. parapsilosis* |
| Dig-GG CCC GAG CGA ACT AGA CTT TT | SEQ ID NO: 21 | ITS2 reuion of *C. krusei* |
| Dig-CC CGG CCT TAC AAC AAC CAA AC | SEQ ID NO: 22 | ITS2 region of *C. guilliermondii* |
| Dig-AG TTA AGC TTG TTA CAG ACT CA | SEQ ID NO: 23 | ITS2 region of *C. rugosa* |
| Dig-AC TCG TTA TTT TCC AGA CAG AC | SBQ ID NO: 24 | ITS2 region of *C. utilis* |
| Dig-TC GTT GAC CAG TAT AGT ATT TG | SEQ ID NO: 25 | ITS2 region of *C. zeylanoides* |
| Dig-CC GTT GGT GGA TTT GTT TCT AA | SEQ ID NO: 26 | ITS2 region of *C. haemulonii* |
| Dig-AA AGC GAG GGG CCT TCT GCG CG | SEQ ID NO: 27 | ITS2 region of *C. lambica* |
| Dig-GC GAG GGG CCT TCT GCG CGA AC | SEQ ID NO: 28 | ITS2 region of *C. lambica* |
| Dig-GA GAC TCA TAG GTG TCA TAA AG | SEQ ID NO: 29 | ITS2 region of *C. kefyr* |
| Dig-CT ACC AAA ACG CTT GTG CAG TC | SEQ ID NO: 30 | ITS2 region of *C. viswanathii* |
| Dig-CT CCG AAA TAT CAA CCG CGC TG | SEQ ID NO: 31 | ITS2 region of *C. lusitaneae* |
| Dig-AC GAG CGT CTG CTG GCT CCA CA | SEQ ID NO: 32 | ITS2 region of *C. norvegica* |
| Dig-AC TGA GCG AAG TAC ACA ACA CT | SEQ ID NO: 33 | ITS2 region of *C. norvegensis* |
| Dig-AT CAG CTA GGC AGG TTT AGA AG | SEQ ID NO: 34 | ITS2 region of *C. pelliculosa* |
| Dig-AA GGC GGT CTC TGG CGT CGC CC | SEQ ID NO: 35 | ITS2 region of *C. dubliniensis* |

*Dig = digoxigenin label

PCR Amplification

The reaction mixture (100 μl) contained 10 μl of 10× PCR buffer [100 mM Tris-HCl, pH 8.3, 500 mM KCl (Boehringer Mannheim, Indianapolis, Ind.)], 6 μl of 25 mM $MgCl_2$, 8 μl of deoxynucleotide triphosphate mix (1.25 mM each of dATP, dCTP, dGTP, and dTTP), 1 μl of each primer (20 μM), 2.5 U of Taq DNA polymerase (TaKaRa Shuzo Co., Ltd., Shiga, Japan), 2 μl of template DNA (0.5 ng/μl), and sterile water to make the total volume 100 μl. Vials were placed in the heating block of a Model 9600 thermal cycler (Perkin-Elmer, Emeryville, Calif.) after it reached 95° C. PCR amplification conditions were: 5 minutes denaturation at 95° C., followed by 30 cycles of 95° C. for 30 seconds, 58° C. for 30 seconds, and 72° C. for 1 minute. A final extension step was conducted at 72° C. for 5 minutes. After amplification, samples were stored at 4° C. for not more than 20 hours before use in the EIA. Appropriate positive and negative controls were included and PCR contamination precautions were followed in accordance with the method of Kwok, S., et al., 1989. Avoiding false positives with PCR. *Nature* (London) 339:237–238; and Fujita, et al., 1995, *J. Clin. Microbiol.* 33:962–967.

Agarose Gel Electrophoresis

Electrophoresis was conducted in TBE (0.1 M Tris, 0.09 M boric acid, 0.001 M EDTA, pH 8.4) buffer at 76 volts for approximately 1 hour using gels composed of 1% (wt/vol) agarose (Boehringer Mannheim) and 1% (wt/vol) NuSieve (FMC Bioproducts, Rockland, Me.). Gels were stained with 0.5 μg of Et Br per ml of deionized water for 30 minutes followed by a 30 minute wash in deionized water. Gels were viewed with a UV illuminator and photographed.

PCR-EIA

PCR-amplified DNA was hybridized to species-specific digoxigenin-labeled probes and to an all-Candida species biotinylated probe, and the complex was added to streptavidin-coated microtitration plates and trapped. Then, an indirect EIA was conducted as described by Fujita, et al., 1995, *J. Clin. Microbiol.* 33:962–967, and Shin, et al. 1997, *J. Clin. Micro.* 35:1454–1459. All probes were tested in a checkerboard manner against DNA from other Candida species as well as against DNA from other fungal organisms.

To facilitate hybridization, single-stranded DNA was prepared from double-stranded PCR products by heat denaturation. A thin-walled polypropylene (0.5 ml) vial with flat cap (Perkin-Elmer), containing 10 μl of the PCR product plus 10 μl of sterile distilled water was heated at 95° C. for 5 minutes and then immediately cooled on ice. Two hundred microliters of hybridization solution containing 4× SSC (saline-sodium citrate buffer; 0.6 M NaCl, 0.06 M trisodium citrate, pH 7.0), 20 mM HEPES, 2 mM EDTA, and 0.15% (vol/vol) Tween 20 supplemented with 50 ng/ml each of biotin- and digoxigenin-labeled probes were then added to the single-stranded DNA.

After hybridization at 37° C. for 1 hour, 100 μl of each sample was added to duplicate wells of a streptavidin-coated microtitration plate (Boehringer Mannheim), and the plate was incubated at ambient temperature for 1 hour with shaking (Minishaker, manufactured for Dynatech by CLTI, Middletown, N.Y.). After washing six times with 0.01 M potassium phosphate buffered saline, pH 7.2, containing 0.05% Tween 20 (PBST), 100 μl of horseradish peroxidase-conjugated, anti-digoxigenin Fab fragment (Boehringer Mannheim), diluted 1:1000 in hybridization buffer, was added to each well. After a 30 minute incubation at ambient temperature on the shaker, the plate was again washed six times with PBST. Each well then received 100 μl of a mixture of one volume of 3, 3', 5, 5'-tetramethylbenzidine peroxidase substrate (Kirkegaard & Perry Laboratories, Inc., Gaithersburg, Md.) and one volume of peroxidase solution (Kirkegaard & Perry). The plate was kept at ambient temperature for 15 minutes, and the $A_{650\ nm}$ of each well was determined with a microtitration plate reader (UV Max; Molecular Devices, Inc., Menlo Park, Calif.). The absorbance of a reagent blank in which target DNA was replaced with distilled water was subtracted from each test sample.

Statistical Analyses

The student's t-test was used to determine significant differences between absorbance values of homologous and non-homologous probe reactions. Absorbance values for all probes versus their homologous DNA were significantly different from those with non-homologous DNA (P<0.05) except for the cross-reactivity of the C. guillermondii probe with C. zeylanoides DNA and the C. glabrata probe with S. cerevisiae DNA (P>0.05, FIGS. 1 and 2).

EXAMPLE 3

Specificity of Digoxigenin-Labeled Probes

Eighteen species-specific DNA probes were designed and tested for hybridization specificity. The results are shown in FIGS. 1 and 2. Absorbance values for all probes versus their homologous DNA were significantly different from those with non-homologous DNA, (P<0.05) except in two cases of cross-reactivity of the C. guillermondii probe with C. zeylanoides DNA and the C. glabrata probe with S. cerevisiae DNA (P>0.05, FIGS. 1 and 2). However, the probe for C. zeylanoides (Cz) did not hybridize with DNA from C. guilliermondii, so that by a process of elimination these probes could be used to specifically identify the Candida species. In the other case, the previously published (Fujita, et al., 1995, *J. Clin. Microbiol.* 33:962–967; Shin, et al. 1997, *J. Clin. Micro.* 35:1454–1459) probe for C. glabrata, Cg, cross-hybridized with Saccharomyces cerevisiae DNA. This probe for C. glabrata also cross-hybridized with Candida species not previously tested, i.e. C. pelliculosa, and C. utilis (P>0.05). Therefore, the Cg probe was redesigned (Cge) resulting in the elimination of cross-hybridizations with all above mentioned species except for S. cerevisiae.

Multiple strains of several species were tested. Absorbance values were consistent among the strains of each species except in two cases as shown in Table 3. Absorbance values for the C. parapsilosis probe (Cp) versus C. parapsilosis Lehmann Group III (Lin, D., L.-C. et al., 1995. Three distinct genotypes within *Candida parapsilosis* from clinical sources. *J. Clin. Micro.* 33:1815–1821) and the Ch probe for C. haemulonii versus one strain (C. haemulonii 90.00.3593) gave statistically lower values than for positive control samples using homologous DNA. These discrepant cases may indicate a finer taxonomic discrimination of isolates by genotypic compared to phenotypic methods (Lehmnann, P. F., et al., 1993. Unrelatedness of groups of yeasts within the *Candida haemulonii* complex. *J. Clin. Micro.* 31:1683–1687; Zeng, S., et al., 1996. Random amplified polymorphic DNA analysis of culture collection strains of Candida species. *J. Med. Vet. Mycol.* 34:293–297; and Lin, et al., 1995, *J. Clin. Micro.* 33:1815–1821).

In Table 3, strains designated in bold print were those which were sequenced and from which the species-specific probe was designed.

TABLE 3

Consistency of $A_{650nm}$ Values for Multiple Isolates Within a Given Species

| SPECIES (PROBE) | ISOLATE | MEAN $A_{650nm}$ ± S.D.[a] | |
|---|---|---|---|
| | | For Each Isolate | For Each Species |
| C. tropicalis (CT) | CDC 38 | 0.870 ± 0.354 | 1.038 ± 0.238 |
| | ATCC 750 | 1.206 ± 0.066 | |
| C. guilliermondii (GU) | ATCC 6260 | 0.821 ± 0.303 | 1.162 ± 0.256 |
| | ATCC 34134 | 1.464 ± 0.188 | |
| | KOR G1 | 1.025 ± 0.355 | |
| | B4346 | 1.152 ± 0.396 | |
| | B4347 | 1.349 ± 0.402 | |
| C. rugosa (CR) | ATCC 10571 | 0.222 ± 0.098 | 0.239 ± 0.028 |
| | ATCC 38772 | 0.271 ± 0.077 | |
| | ATCC 58964 | 0.223 ± 0.069 | |
| C. utilis (CU2) | ATCC 22023 | 1.161 ± 0.193 | 1.198 ± 0.053 |
| | ATCC 64882 | 1.236 ± 0.416 | |
| C. zeylanoides (CZ) | ATCC 7351 | 0.361 ± 0.170 | 0.433 ± 0.104 |
| | B996 | 0.466 ± 0.110 | |
| | B997 | 0.339 ± 0.170 | |
| | B4232 | 0.565 ± 0.060 | |
| C. lambica (LA) | ATCC 24750 | 0.640 ± 0.175 | 0.677 ± 0.052 |
| | ATCC 22695 | 0.714 ± 0.170 | |
| C. kefyr (KF) | ATCC 46764 | 1.184 ± 0.384 | 1.282 ± 0.166 |
| | ATCC 66028 | 1.474 ± 0.208 | |
| | ATCC 42265 | 1.187 ± 0.224 | |
| C. lusitaniae (LU) | ATCC 34449 | 0.483 ± 0.162 | 0.539 ± 0.079 |
| | ATCC 42720 | 0.595 ± 0.148 | |
| C. norvegensis (NS) | ATCC 22977 | 0.716 ± 0.242 | 0.630 ± 0.122 |
| | ATCC 32816 | 0.544 ± 0.164 | |
| C. pelliculosa (PL) | ATCC 8168 | 0.624 ± 0.320 | 0.642 ± 0.086 |
| | KOR P1 | 0.809 ± 0.242 | |
| | KOR P2 | 0.574 ± 0.170 | |
| | KOR P4 | 0.612 ± 0.106 | |
| | KOR P5 | 0.587 ± 0.152 | |
| | KOR P6 | 0.649 ± 0.156 | |
| C. parapsilosis (CP) | ATCC 22019 | 0.493 ± 0.231 | |
| Group I | MCO478 | 0.554 ± 0.228 | 0.484 ± 0.061 |
| | MCO441 | 0.453 ± 0.199 | |
| | MCO433 | 0.445 ± 0.173 | |
| Group II | MCO456 | 0.455 ± 0.243 | 0.489 ± 0.041 |
| | MCO462 | 0.478 ± 0.203 | |
| | MCO471 | 0.534 ± 0.133 | |
| Group III | MCO429 | 0.162 ± 0.058 | 0.158 ± 0.006 |
| | MCO448 | 0.154 ± 0.072 | |
| C. haemulonii (CH) | ATCC 22991 | 0.841 ± 0.332 | |
| | CBS 5199 | 0.850 ± 0.082 | |
| Variant | 90.00.3593 | 0.088 ± 0.026 | |

[a]Mean $A_{650nm}$ ± standard deviation for n = 2 to 5 experiments conducted in duplicate Species-specific probes were designed to identify two species that share a common phenotype, namely C. albicans and C. dubliniensis. The new species, C. dubliniensis, has been described by Sullivan, D. J., et al., 1995, Candida dubliniensis sp. nov.: phenotypic and molecular characterization of a novel species associated with oral candidiasis in HIV-infected individuals. *Microbiology* 141:1507–1521. By routine conventional phenotypic methods, C. dubliniensis is identified as C. albicans. The probes designed in this example discriminated C. albicans from C. dubliniensis as shown in Table 4, below. The Ca probe which detects C. albicans did not react with DNA from C. dubliniensis strains and the Db probe for C. dubliniensis did not hybridize with DNA from C. albicans.

The data shown in Table 4 demonstrate that the sequences of the ITS2 regions for C. albicans and C. dubliniensis differ. Specific probes for each species provide a rapid method to differentiate microorganisms having virtually the same phenotype but which differ genotypically.

TABLE 4

Differentiation of C. albicans from C. dubliniensis
By Species-specific Probes.

| TARGET DNA | C. albicans Probe | C. dubliniensis Probe |
|---|---|---|
| *C. albicans* | | |
| ATCC 11006 (stellatoidea) | 0.485 ± 0.252[a] | 0 |
| ATCC 20408 (stellatoidea) | 0.370 ± 0.168 | 0 |
| ATCC 36232 (stellatoidea) | 0.409 ± 0.178 | 0 |
| B36 | 0.568 ± 0.236 | 0 |
| Q10 | 0.640 ± 0.192 | 0 |
| Lecog | 0.464 ± 0.124 | 0 |
| 2730 | 0.631 ± 0.192 | 0 |
| 3153A | 0.528 ± 0.068 | 0 |
| Mean $A_{650nm}$ for CA Probe | 0.512 ± 0.095 | 0 |
| *C. dubliniensis* | | |
| M1 | 0 | 0.351 ± 0.090 |
| M4 | 0 | 0.407 ± 0.186 |
| P30 | 0 | 0.346 ± 0.088 |
| 1419-2 | 0 | 0.402 ± 0.132 |
| 901013 | 0 | 0.393 ± 0.101 |
| Mean $A_{650nm}$ for DB Probe | 0 | 0.380 ± 0.029 |

[a]Mean $A_{650nm}$ ± standard deviation for n = 2 to 5 experiments conducted in duplicate The probes described herein extend the range of Candida probes to include a test matrix of 18 Candida species. This test matrix is capable of complementing species identification by the API20C carbohydrate assimilation system. The probes described herein are species-specific and can be used to identify cultures Candida species including *C. dubliniensis* which cannot currently be differentiated from *C. albicans* by routine phenotypic methods.

Standardization of DNA extraction for all Candida species is facilitated by using broth culture and a commercially available extraction kit. The PCR-EIA for identification requires less time (one day) than conventional methods which require an average of 3 to 5 days for species identification of most Candida spp. and can require up to 4 or 5 weeks for unusual species such as *C. norvegensis* or *C. utilis*. Since choice of drug varies from species to species, an accurate and timely identification is important so that appropriately targeted therapy can be administered to a patient. Some species are innately resistant to certain drugs, i.e. *C. krusei* to fluconazole, so that when an identification of "Candida spp other than *albicans*" is made, it may be an inadequate guide to the selection of appropriate therapy.

*C. dubliniensis* has been recently described as a new species after it was found that some "*albicans*" strains did not behave as typical *C. albicans* by molecular methods. DNA from these strains, when probed with *C. albicans*-specific and mid-repetitive elements such as Ca3 or 27A, did not react positively. Molecular differences became apparent by sequencing the ITS2 region of both species, and probes were designed that hybridized only with their homologous DNA.

It should be understood that the foregoing relates only to preferred embodiments of the present invention, and that numerous modifications or alterations may be made therein without departing from the spirit and the scope of the invention as set forth in the appended claims. All of the references cited in this Specification are hereby incorporated by reference in their entireties.

We claim:

1. A nucleic acid probe for a Candida species, wherein the probe selectively hybridizes with a nucleic acid molecule encoding a portion of the internal transcribed spacer 2 region, or a complementary sequence thereof, of a Candida species selected from the group consisting of C. haemulonii, C. kefyr, C. lambica, C. lusitaniae, C. norvegensis, C. norvegica, C. rugosa, C. utilis, C. viswanathii, C. zeylanoides, C. dubliniensis, and C. pelliculosa, wherein the nucleic acid probe selectively hybridizes to a species-specific portion of a Candida internal transcribed spacer region nucleic acid, and does not hybridize with other nucleic acids so as to prevent determination of an adequate positive hybridization to the species-specific portion of the Candida internal transcribed spacer region.

2. The nucleic acid probe of claim 1, wherein the internal transcribed spacer 2 region comprises the sequence set forth in SEQ ID NO:2, or a complementary sequence thereof, of a C. haemulonii.

3. The nucleic acid probe of claim 2, having a nucleic acid sequence of SEQ ID NO:26, or a complementary sequence thereof.

4. The nucleic acid probe of claim 1, wherein the internal transcribed spacer 2 region comprises the sequence set forth in SEQ ID NO:3, or a complementary sequence thereof, of a C. kefyr.

5. The nucleic acid probe of claim 4, having a nucleic acid sequence of SEQ ID NO:29, or a complementary sequence thereof.

6. The nucleic acid probe of claim 1, wherein the internal transcribed spacer 2 region comprises the sequence set forth in SEQ ID NO:4, or a complementary sequence thereof, of a C. lambica.

7. The nucleic acid probe of claim 6, having a nucleic acid sequence of SEQ ID NO:27 or SEQ ID NO:28, or a complementary sequence thereof.

8. The nucleic acid probe of claim 1, wherein the internal transcribed spacer 2 region comprises the sequence set forth in SEQ ID NO:5, or a complementary sequence thereof, of a C. lusitaniae.

9. The nucleic acid probe of claim 8, having a nucleic acid sequence of SEQ ID NO:31, or a complementary sequence thereof.

10. The nucleic acid probe of claim 1, wherein the internal transcribed spacer 2 region comprises the sequence set forth in SEQ ID NO:6, or a complementary sequence thereof, of a C. norvegensis.

11. The nucleic acid probe of claim 10, having a nucleic acid sequence of SEQ ID NO:33, or a complementary sequence thereof.

12. The nucleic acid probe of claim 1, wherein the internal transcribed spacer 2 region comprises the sequence set forth in SEQ ID NO:7, or a complementary sequence thereof, of a C. norvegica.

13. The nucleic acid probe of claim 12, having a nucleic acid sequence of SEQ ID NO:32, or a complementary sequence thereof.

14. The nucleic acid probe of claim 1, wherein the internal transcribed spacer 2 region comprises the sequence set forth in SEQ ID NO:8, or a complementary sequence thereof, of a C. rugosa.

15. The nucleic acid probe of claim 14, having a nucleic acid sequence of SEQ ID NO:23, or a complementary sequence thereof.

16. The nucleic acid probe of claim 1, wherein the internal transcribed spacer 2 region comprises the sequence set forth in SEQ ID NO:9, or a complementary sequence thereof, of a C. utilis.

17. The nucleic acid probe of claim 16, having a nucleic acid sequence of SEQ ID NO:24, or a complementary sequence thereof.

18. The nucleic acid probe of claim 1, wherein the internal transcribed spacer 2 region comprises the sequence set forth in SEQ ID NO:10, or a complementary sequence thereof, of a *C. viswanathii*.

19. The nucleic acid probe of claim 18, having a nucleic acid sequence of SEQ ID NO:30, or a complementary sequence thereof.

20. The nucleic acid probe of claim 1, wherein the internal transcribed spacer 2 region comprises the sequence set forth in SEQ ID NO:11, or a complementary sequence thereof, of a *C. zeylanoides*.

21. The nucleic acid probe of claim 20, having a nucleic acid sequence of SEQ ID NO:25, or a complementary sequence thereof.

22. The nucleic acid probe of claim 1, wherein the internal transcribed spacer 2 region comprises the sequence set forth in SEQ ID NO:12, or a complementary sequence thereof, of a *C. dubliniensis*.

23. The nucleic acid probe of claim 22, having a nucleic acid sequence of SEQ ID NO:35, or a complementary sequence thereof.

24. The nucleic acid probe of claim 1, wherein the internal transcribed spacer 2 region comprises the sequence set forth in SEQ ID NO:13, or a complementary sequence thereof, of a *C. pelliculosa*.

25. The nucleic acid probe of claim 24, having a nucleic acid sequence of SEQ ID NO:34, or a complementary sequence thereof.

26. A method for detecting a species of Candida in a sample comprising a) combining the sample with a nucleic acid probe for a Candida species, wherein the probe selectively hybridizes with a nucleic acid molecule encoding a portion of the internal transcribed spacer 2 region, or a complementary sequence thereof, of a Candida species selected from the group consisting of *C. haemulonii, C. kefyr, C. lambica, C. lusitaniae, C. norvegensis, C. norvegica, C. rugosa, C. utilis, C. viswanathii, C. zeylanoides, C. dubliniensis,* and *C. pelliculosa,* wherein the nucleic acid probe selectively hybridizes to a species-specific portion of a Candida internal transcribed spacer region nucleic acid, and does not hybridize with other nucleic acids so as to prevent determination of an adequate positive hybridization to the species-specific portion of the Candida internal transcribed spacer region; and, b) detecting the presence of hybridization, the presence of hybridization indicating the respective Candida species in the sample.

27. The method of claim 26, wherein the internal transcribed spacer 2 region comprises the sequence set forth in SEQ ID NO:2, or a complementary sequence thereof, of a *C. haemulonii*.

28. The method of claim 27, having a nucleic acid sequence of SEQ ID NO:26, or a complementary sequence thereof.

29. The method of claim 26, wherein the internal transcribed spacer 2 region comprises the sequence set forth in SEQ ID NO:3, or a complementary sequence thereof, of a *C. kefyr*.

30. The method of claim 29, having a nucleic acid sequence of SEQ ID NO:29, or a complementary sequence thereof.

31. The method of claim 26, wherein the internal transcribed spacer 2 region comprises the sequence set forth in SEQ ID NO:4, or a complementary sequence thereof, of a *C. lambica*.

32. The method of claim 31, having a nucleic acid sequence of SEQ ID NO:27 or SEQ ID NO:28, or a complementary sequence thereof.

33. The method of claim 26, wherein the internal transcribed spacer 2 region comprises the sequence set forth in SEQ ID NO:5, or a complementary sequence thereof, of a *C. lusitaniae*.

34. The method of claim 33, having a nucleic acid sequence of SEQ ID NO:31, or a complementary sequence thereof.

35. The method of claim 26, wherein the internal transcribed spacer 2 region comprises the sequence set forth in SEQ ID NO:6, or a complementary sequence thereof, of a *C. norvegensis*.

36. The method of claim 35, having a nucleic acid sequence of SEQ ID NO:33, or a complementary sequence thereof.

37. The method of claim 26, wherein the internal transcribed spacer 2 region comprises the sequence set forth in SEQ ID NO:7, or a complementary sequence thereof, of a *C. norvegica*.

38. The method of claim 37, having a nucleic acid sequence of SEQ ID NO:32, or a complementary sequence thereof.

39. The method of claim 26, wherein the internal transcribed spacer 2 region comprises the sequence set forth in SEQ ID NO:8, or a complementary sequence thereof, of a *C. rugosa*.

40. The method of claim 39, having a nucleic acid sequence of SEQ ID NO:23, or a complementary sequence thereof.

41. The method of claim 26, wherein the internal transcribed spacer 2 region comprises the sequence set forth in SEQ ID NO:9, or a complementary sequence thereof, of a *C. utilis*.

42. The method of claim 41, having a nucleic acid sequence of SEQ ID NO:24, or a complementary sequence thereof.

43. The method of claim 26, wherein the internal transcribed spacer 2 region comprises the sequence set forth in SEQ ID NO:10, or a complementary sequence thereof, of a *C. viswanathii*.

44. The method of claim 43, having a nucleic acid sequence of SEQ ID NO:30, or a complementary sequence thereof.

45. The method of claim 26, wherein the internal transcribed spacer 2 region comprises the sequence set forth in SEQ ID NO:11, or a complementary sequence thereof, of a *C. zeylanoides*.

46. The method of claim 45, having a nucleic acid sequence of SEQ ID NO:25, or a complementary sequence thereof.

47. The method of claim 26, wherein the internal transcribed spacer 2 region comprises the sequence set forth in SEQ ID NO:12, or a complementary sequence thereof, of a *C. dubliniensis*.

48. The method of claim 47, having a nucleic acid sequence of SEQ ID NO:35, or a complementary sequence thereof.

49. The method of claim 26, wherein the internal transcribed spacer 2 region comprises the sequence set forth in SEQ ID NO:13, or a complementary sequence thereof, of a *C. pelliculosa*.

50. The method of claim 49, having a nucleic acid sequence of SEQ ID NO:34, or a complementary sequence thereof.

\* \* \* \* \*

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
      (A) LENGTH: 192 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Candida guilliermondi (xi) SEQUENCE DESCRIPTION: SEQ ID NO:1:

```
CTCTCTCAAA CCCCCGGGTT TGGTATTGAG TGATACTCTT AGTCGGACTA GGCGTTTGCT      60

TGAAAAGTAT TGGCATGGGT AGTATGGATA GTGCTGTCGA CCTCTCAATG TATTAGGTTT     120

ATCCAACTCG TTGAATGGTG TGGCGGGATA TTTCTGGTAT TGTTGGCCCG GCCTTACAAC     180

AACCAAACAA GC                                                         192
```

(2) INFORMATION FOR SEQ ID NO:2:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Candida haemulonii (xi) SEQUENCE DESCRIPTION: SEQ ID NO:2:

```
GAGCGTGATA TCTTCTCACC GTTGGTGGAT TTGTTTCTAA ATATCATGCC ACAGTGAAGT      60

CTACGC                                                                66
```

(2) INFORMATION FOR SEQ ID NO:3:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Candida keyfr (xi) SEQUENCE DESCRIPTION: SEQ ID NO:3:

```
CTCTCTCAAA CCTTTGGGTT TGGTAGTGAG TGATACTCGT CTCGGGCTTA ACTTGAAAGT      60

GGCTAACCGT TGCCATCTGC GTGAGCAGGC TGCGTGTCAA GTCTATGGAC TCGACTCTTG     120

CACATCTACG TCTTAAGTAT GCGCCAATTC GTGGTAAGCT TGGGTCATAG AGACTCATAG     180

GTGTTATAAA GACTCGCTGG TGTTTGTCTC CTTGAGGCAT ACGGCTTTAC AACTCTCAAG     240
```

(2) INFORMATION FOR SEQ ID NO:4:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Candida lambica (xi) SEQUENCE DESCRIPTION: SEQ ID NO:4:

```
CCTTCTTGGA GCGGTGCTTC AGACCTGGCG GGCTGTCTTT TTGGACGGCG CGCCCAAAGC      60

GAGGGGCCTT CTGCGCGAAC TAGACTGTGC GCGCGGGGCG GTCGGCGAAC TTATTACCAA     120

G                                                                    121
```

(2) INFORMATION FOR SEQ ID NO:5:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida lusitaniae (xi) SEQUENCE DESCRIPTION: SEQ ID NO:5:

```
GAGCGTCGCA TCCCCTCTAA CCCCCGGTTA GGCGTTGCTC CGAAATATCA ACCGCGCTGT    60

CAAATACG                                                             68
```

(2) INFORMATION FOR SEQ ID NO:6:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida norvegensis (xi) SEQUENCE DESCRIPTION: SEQ ID NO:6:

```
CCTTCTTGCG CAAGCAGAAG TTGGGGTTGC CACGGCCCGT GCGGCCTGTG TGTGGCTCCC    60

CGAAACGGAA CGGCAGCGGG ACTGAGCGAA GTACACAACA CTCGCGCTTG GCCCGCCGAA   120

CTTTTTTTTA ATCTAAG                                                  137
```

(2) INFORMATION FOR SEQ ID NO:7:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida norvegica (xi) SEQUENCE DESCRIPTION: SEQ ID NO:7:

```
CCTTCTCAAG CGTGAGCTTG GTGTTGGCGG AGGTCTTTCG AGGCCCCGCT GAAATACGCA    60

GGGGGTGCGT GGAAACGAGC TTTCTCTCTA CTAATGTCTA GTTCTGCCAA CTCATTGGAC   120

GAGCGTCTGC TGGCTCCACA ATCCCACCCC CATTACCCCA AC                      162
```

(2) INFORMATION FOR SEQ ID NO:8:

(i) SEQUENCE CHARACTERISTICS:

(A) LENGTH: 89 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida rugosa (xi) SEQUENCE DESCRIPTION: SEQ ID NO:8:

CTCTCTCGCA AGTGTTGGCA CCACGCCGGC AGGCGTCTGC CCGAAACGCG ACCGTCTAAA    60

ACAGTTAAGC TTGTTACAGA CTCACGATC    89

(2) INFORMATION FOR SEQ ID NO:9:

(i) SEQUENCE CHARACTERISTICS:
        (A) LENGTH: 183 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida utilis (xi) SEQUENCE DESCRIPTION: SEQ ID NO:9:

CTCTCTCAAG ATCCTCTAGG GGACTTGGTA TTGAGTGATA CTCTGTGTTA ACTTGAAATA    60

CTCTAGGCAG AGCTCCCCCC TGGAAATCCT CTGGGCCGAA ATAATGTATT AGGTTCTACC   120

AACTCGTTAT TTTCCAGACA GACTTCCAGG CAGAGCTCGT GCCCCTAACA TAGCAGTCTA   180

AGC    183

(2) INFORMATION FOR SEQ ID NO:10:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida viswanathii (xi) SEQUENCE DESCRIPTION: SEQ ID NO:10:

CTCCCTCAAC CCCGCGGGTT TGGTGTTGAG CAATACGCCA GGTTTGTTTG AAAGACGTAC    60

GTGGAGACAA TATTAGCGAC TTAGGTTCTA CCAAAACGCT TGTGCAGTCG GTCCCACACA   120

CAGTGTAAGC TAACA   135

(2) INFORMATION FOR SEQ ID NO:11:

(i) SEQUENCE CHARACTERISTICS:
        (A) LENGTH: 187 base pairs (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                (A) ORGANISM: Candida zeylanoides (xi) SEQUENCE DESCRIPTION: SEQ ID NO:11:

```
CTCTCTCAAA TCTTCGGATT TGGTTTTGAG TGATACTCTT AGTCAGACTA AGCGTTTGCT      60

TGAAATGTAA TGGCATGAGT GGTACTAGAT AGTGCTGAAC TGTCGTCATG TATTAGGTTT     120

ATCCAACTCG TTGACCAGTA TAGTATTTGT TTATTACACA GGCTCGGCCT TACAACAACA     180

AACAAAG                                                               187
```

(2) INFORMATION FOR SEQ ID NO:12:

(i) SEQUENCE CHARACTERISTICS:
                (A) LENGTH: 156 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                (A) ORGANISM: Candida dubliniensis (xi) SEQUENCE DESCRIPTION: SEQ ID NO:12:

```
CTCCCTCAAA CCCCTAGGGT TTGGTGTTGA GCAATACGAC TTGGGTTTGC TTGAAAGATG      60

ATAGTGGTAT AAGGCGGAGA TGCTTGACAA TGGCTTAGGT GTAACCAAAA ACATTGCTAA     120

GGCGGTCTCT GGCGTCGCCC ATTTTATTCT TCAAAC                               156
```

(2) INFORMATION FOR SEQ ID NO:13:

(i) SEQUENCE CHARACTERISTICS:
                (A) LENGTH: 188 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                (A) ORGANISM: Candida pelliculosa (xi) SEQUENCE DESCRIPTION: SEQ ID NO:13:

```
CTCTCTCAAA CCTTCGGGTT TGGTATTGAG TGATACTCTG TCAAGGGTTA ACTTGAAATA      60

TTGACTTAGC AAGAGTGTAC TAATAAGCAG TCTTTCTGAA ATAATGTATT AGGTTCTTCC     120

AACTCGTTAT ATCAGCTAGG CAGGTTTAGA AGTATTTTAG GCTCGGCTTA ACAACAATAA     180

ACTAAAAG                                                              188
```

(2) INFORMATION FOR SEQ ID NO:14:

```
      (i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (ix) FEATURE:
          (A) NAME/KEY: misc_feature
          (B) LOCATION: 1..20
          (D) OTHER INFORMATION: /note= "ITS3 5.8S rDNA universal 5'
              primer"

(xi) SEQUENCE DESCRIPTION: SEQ ID NO:14:

GCATCGATGA AGAACGCAGC                                                   20

(2) INFORMATION FOR SEQ ID NO:15:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (ix) FEATURE:
          (A) NAME/KEY: misc_feature
          (B) LOCATION: 1..20
          (D) OTHER INFORMATION: /note= "ITS4 28S rDNA universal 3'
              primer"

(xi) SEQUENCE DESCRIPTION: SEQ ID NO:15:

TCCTCCGCTT ATTGATATGC                                                   20

(2) INFORMATION FOR SEQ ID NO:16:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (ix) FEATURE:
          (A) NAME/KEY: misc_feature
          (B) LOCATION: 1..21
          (D) OTHER INFORMATION: /note= "5'-end labeled,
              biotinylated probe; 5.8S rDNA"

(xi) SEQUENCE DESCRIPTION: SEQ ID NO:16:

CATGCCTGTT TGAGCGTCRT T                                                 21

(2) INFORMATION FOR SEQ ID NO:17:

(i) SEQUENCE CHARACTERISTICS:
          (A) LENGTH: 22 base pairs
          (B) TYPE: nucleic acid
```

```
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Candida albicans (ix) FEATURE:
            (A) NAME/KEY: misc_feature
            (B) LOCATION: 1..22
            (D) OTHER INFORMATION: /note= "CA probe of ITS region"

(xi) SEQUENCE DESCRIPTION: SEQ ID NO:17:

ATTGCTTGCG GCGGTAACGT CC                                                  22

(2) INFORMATION FOR SEQ ID NO:18:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Candida tropicalis (ix) FEATURE:
            (A) NAME/KEY: misc_feature
            (B) LOCATION: 1..22
            (D) OTHER INFORMATION: /note= "CT probe of ITS region"

(xi) SEQUENCE DESCRIPTION: SEQ ID NO:18:

AACGCTTATT TTGCTAGTGG CC                                                  22

(2) INFORMATION FOR SEQ ID NO:19:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Candida glabrata (ix) FEATURE:
            (A) NAME/KEY: misc_feature
            (B) LOCATION: 1..22
            (D) OTHER INFORMATION: /note= "CGE probe of ITS region"

(xi) SEQUENCE DESCRIPTION: SEQ ID NO:19:

TTTACCAACT CGGTGTTGAT CT                                                  22

(2) INFORMATION FOR SEQ ID NO:20:

(i) SEQUENCE CHARACTERISTICS:
```

(A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida parapsilosis (ix) FEATURE:
        (A) NAME/KEY: misc_feature
        (B) LOCATION: 1..22
        (D) OTHER INFORMATION: /note= "CP probe of ITS region"

(xi) SEQUENCE DESCRIPTION: SEQ ID NO:20:

ACAAACTCCA AAACTTCTTC CA                                              22

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida krusei (ix) FEATURE:
        (A) NAME/KEY: misc_feature
        (B) LOCATION: 1..22
        (D) OTHER INFORMATION: /note= "CK probe of ITS region"

(xi) SEQUENCE DESCRIPTION: SEQ ID NO:21:

GGCCCGAGCG AACTAGACTT TT                                              22

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida guilliermondii (ix) FEATURE:
        (A) NAME/KEY: misc_feature
        (B) LOCATION: 1..22
        (D) OTHER INFORMATION: /note= "GU probe of ITS region"

(xi) SEQUENCE DESCRIPTION: SEQ ID NO:22:

CCCGGCCTTA CAACAACCAA AC                                              22

(2) INFORMATION FOR SEQ ID NO:23:

```
    (i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida rugosa (ix) FEATURE:
        (A) NAME/KEY: misc_feature
        (B) LOCATION: 1..22
        (D) OTHER INFORMATION: /note= "CR probe of ITS region"

(xi) SEQUENCE DESCRIPTION: SEQ ID NO:23:

AGTTAAGCTT GTTACAGACT CA                                              22

(2) INFORMATION FOR SEQ ID NO:24:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida utilis (ix) FEATURE:
        (A) NAME/KEY: misc_feature
        (B) LOCATION: 1..22
        (D) OTHER INFORMATION: /note= "CU2 probe of ITS region"

(xi) SEQUENCE DESCRIPTION: SEQ ID NO:24:

ACTCGTTATT TTCCAGACAG AC                                              22

(2) INFORMATION FOR SEQ ID NO:25:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida zeylanoides (ix) FEATURE:
        (A) NAME/KEY: misc_feature
        (B) LOCATION: 1..22
        (D) OTHER INFORMATION: /note= "CZ probe of ITS region"

(xi) SEQUENCE DESCRIPTION: SEQ ID NO:25:

TCGTTGACCA GTATAGTATT TG                                              22
```

(2) INFORMATION FOR SEQ ID NO:26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida haemulonii (ix) FEATURE:
        (A) NAME/KEY: misc_feature
        (B) LOCATION: 1..22
        (D) OTHER INFORMATION: /note= "CH probe of ITS region"

(xi) SEQUENCE DESCRIPTION: SEQ ID NO:26:

CCGTTGGTGG ATTTGTTTCT AA                                              22

(2) INFORMATION FOR SEQ ID NO:27:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida lambica (ix) FEATURE:
        (A) NAME/KEY: misc_feature
        (B) LOCATION: 1..22
        (D) OTHER INFORMATION: /note= "Probe LA2 of ITS region"

(xi) SEQUENCE DESCRIPTION: SEQ ID NO:27:

AAAGCGAGGG GCCTTCTGCG CG                                              22

(2) INFORMATION FOR SEQ ID NO:28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida lambica (ix) FEATURE:
        (A) NAME/KEY: misc_feature
        (B) LOCATION: 1..22
        (D) OTHER INFORMATION: /note= "Probe LA4 of ITS region"

(xi) SEQUENCE DESCRIPTION: SEQ ID NO:28:

GCGAGGGGCC TTCTGCGCGA AC                                                      22

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida kefyr (ix) FEATURE:
        (A) NAME/KEY: misc_feature
        (B) LOCATION: 1..22
        (D) OTHER INFORMATION: /note= "KF probe of ITS region"

(xi) SEQUENCE DESCRIPTION: SEQ ID NO:29:

GAGACTCATA GGTGTCATAA AG                                                      22

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida viswanathii (ix) FEATURE:
        (A) NAME/KEY: misc_feature
        (B) LOCATION: 1..22
        (D) OTHER INFORMATION: /note= "VS probe of ITS region"

(xi) SEQUENCE DESCRIPTION: SEQ ID NO:30:

CTACCAAAAC GCTTGTGCAG TC                                                      22

(2) INFORMATION FOR SEQ ID NO:31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida lusitaneae (ix) FEATURE:
        (A) NAME/KEY: misc_feature
        (B) LOCATION: 1..22
        (D) OTHER INFORMATION: /note= "LU probe of ITS region"

(xi) SEQUENCE DESCRIPTION: SEQ ID NO:31:

CTCCGAAATA TCAACCGCGC TG                                                    22

(2) INFORMATION FOR SEQ ID NO:32:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida norvegica (ix) FEATURE:
        (A) NAME/KEY: misc_feature
        (B) LOCATION: 1..22
        (D) OTHER INFORMATION: /note= "NC probe of ITS region"

(xi) SEQUENCE DESCRIPTION: SEQ ID NO:32:

ACGAGCGTCT GCTGGCTCCA CA                                                    22

(2) INFORMATION FOR SEQ ID NO:33:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida norvegensis (ix) FEATURE:
        (A) NAME/KEY: misc_feature
        (B) LOCATION: 1..22
        (D) OTHER INFORMATION: /note= "NS probe of ITS region"

(xi) SEQUENCE DESCRIPTION: SEQ ID NO:33:

ACTGAGCGAA GTACACAACA CT                                                    22

(2) INFORMATION FOR SEQ ID NO:34:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida pelliculosa (ix) FEATURE:
        (A) NAME/KEY: misc_feature
        (B) LOCATION: 1..22

-continued

```
        (D) OTHER INFORMATION: /note= "PL probe of ITS region"

(xi) SEQUENCE DESCRIPTION: SEQ ID NO:34:

ATCAGCTAGG CAGGTTTAGA AG                                              22

(2) INFORMATION FOR SEQ ID NO:35:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Candida dubliniensis (ix) FEATURE:
        (A) NAME/KEY: misc_feature
        (B) LOCATION: 1..22
        (D) OTHER INFORMATION: /note= "DB probe of ITS region"

(xi) SEQUENCE DESCRIPTION: SEQ ID NO:35:

AAGGCGGTCT CTGGCGTCGC CC                                              22
```